United States Patent
Bowles et al.

(10) Patent No.: US 7,095,495 B2
(45) Date of Patent: Aug. 22, 2006

(54) FLUORESCENT INSPECTION OF AIRFOIL COOLING HOLES

(75) Inventors: Gayle M. Bowles, Madisonville, KY (US); Gary E. Wheat, Madisonville, KY (US); William L. Sheyer, Madisonville, KY (US)

(73) Assignee: General Electric Company, Schenectady, NY (US)

( * ) Notice: Subject to any disclaimer, the term of this patent is extended or adjusted under 35 U.S.C. 154(b) by 686 days.

(21) Appl. No.: 10/355,438

(22) Filed: Jan. 31, 2003

(65) Prior Publication Data

US 2004/0149905 A1   Aug. 5, 2004

(51) Int. Cl.
*G01N 21/00* (2006.01)
*B23K 26/00* (2006.01)

(52) U.S. Cl. .............................. 356/237.6; 219/121.71; 219/121.83

(58) Field of Classification Search .. 356/237.1–237.6; 219/121.71, 121.83, 121.85, 121.7; 250/302, 250/459.1
See application file for complete search history.

(56) References Cited

U.S. PATENT DOCUMENTS

| 5,773,790 A | 6/1998 | Moore et al. |
| 2003/0037436 A1* | 2/2003 | Ducotey et al. ........... 29/889.1 |

FOREIGN PATENT DOCUMENTS

| FR | 0359660 | * | 3/1990 |
| GB | 2164746 A | * | 3/1986 |

* cited by examiner

*Primary Examiner*—Hoa Q. Pham
(74) *Attorney, Agent, or Firm*—Andrew Hess; Barbara Joan Haushalter

(57) ABSTRACT

A system and method are provided for inspecting cooling holes of a completed, lasered, and deburred turbine airfoil. The cooling holes are covered with a very porous tape before placing the turbine airfoil into an air fixture that has a metered amount of fluorescent liquid dripped into the airline. The atomized fluorescent liquid flows through the turbine airfoil internal cavities, exiting through the open cooling holes, where it is absorbed by the porous tape. A pattern will appear on the tape surface, in the area of the open holes, indicative of the presence of not-through or plugged cooling holes.

10 Claims, 3 Drawing Sheets

FLUORESCENT INSPECTION OF AIRFOIL COOLING HOLES

BACKGROUND OF THE INVENTION

The present invention relates to gas turbine engines, and, more specifically, to turbine airfoils.

In the manufacture of turbine airfoils, it is often necessary to drill cooling holes through the outer airfoil walls entering the internal air passages. These holes provide a source of cooling air to the airfoil surface during engine operation. Several techniques, such as laser beam drilling, electro-discharge machining, or electro-steam drilling, are used to drill turbine airfoil cooling holes. After the drilling process, the cooling holes must be inspected to determine if they are open to the internal cavities. Methods used to inspect for holes that are not properly drilled through or are plugged include pin-check, by inserting a pin wire into the cooling holes; waterflow inspection; and black light inspection using a beam blocking wax and a fluorescent penetrant mixture.

With the incorporation of laser drill methods that do not require the use of beam blocking wax, manufacturing has become more limited by manual pin-check. Manual insertion of pin wires into 100% of the cooling holes on 100% of all parts processed by laser drilling not only adds cost to the manufacturing process due to the time needed to perform this task, but the pin-check method also presents ergonomic concerns due to repetitive hand motion.

It would be desirable, therefore, to provide an inspection technique that overcomes some of the manufacturing and other limitations of existing cooling hole inspection methods.

BRIEF SUMMARY OF THE INVENTION

The present invention proposes a fluorescent inspection method that is both easier and more efficient to apply than existing methods of detecting not-through and plugged cooling holes. Furthermore, since the proposed fluorescent method does not use wax, it more readily fits into cellular manufacturing.

Accordingly, the present invention provides a system and method for inspecting cooling holes of a completed, lasered, and deburred turbine airfoil. The cooling holes are covered with a very porous tape before splacing the turbine airfoil into an air fixture that has a metered amount of fluorescent liquid dripped into the airline. The atomized fluorescent liquid flows through the turbine airfoil internal cavities, exiting through the open cooling holes, where it is absorbed by the porous tape. A pattern will appear on the tape surface, in the area of the open holes, indicative of the presence of not-through or plugged cooling holes.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
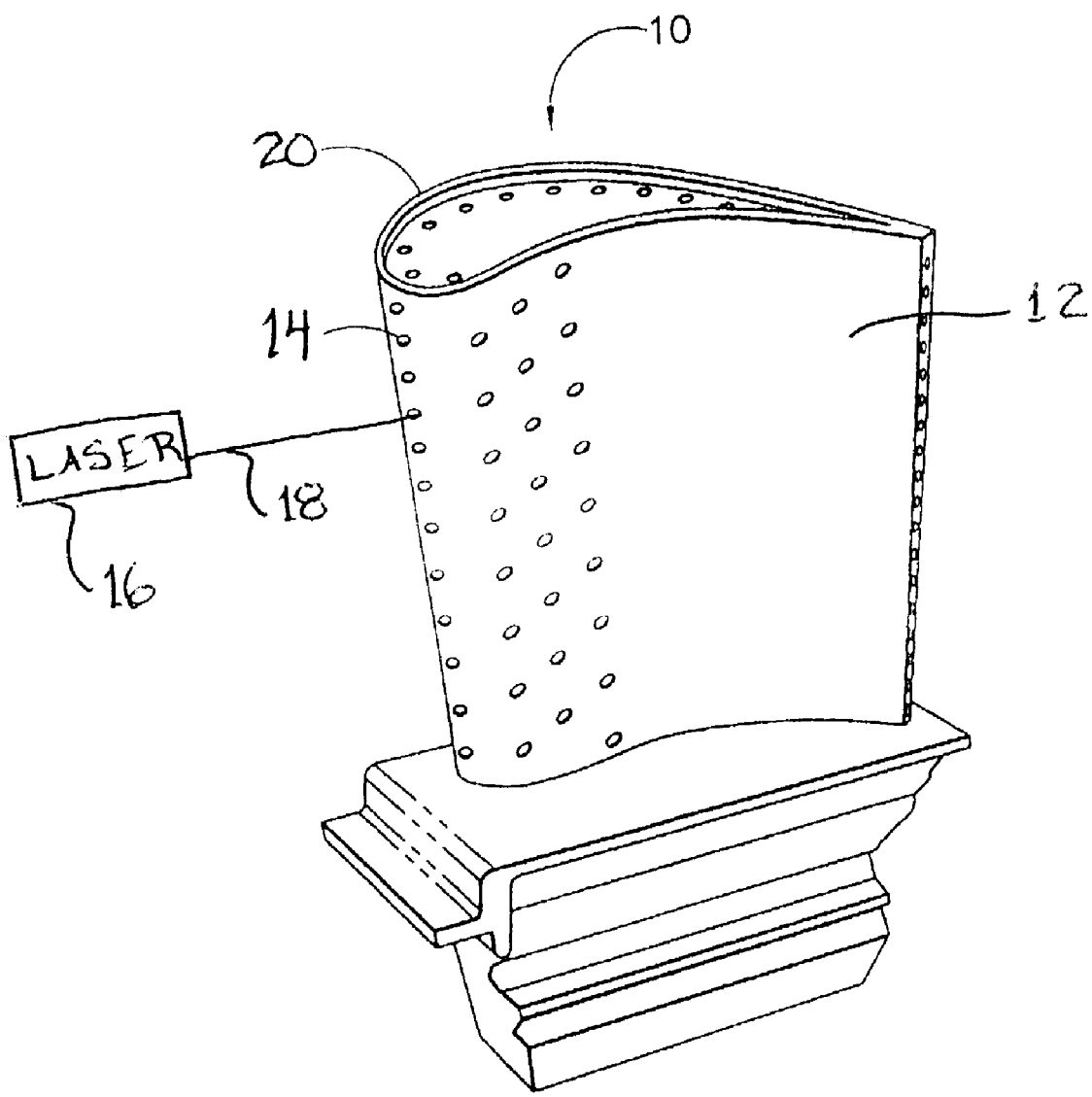
FIG. 1 is a perspective view of a turbine blade illustrating a plurality of cooling holes drilled therein.

Referring to FIG. 1, there is illustrated a gas turbine engine blade 10 and airfoil 12 having a multiplicity of cooling channels or holes 14 formed therein by laser drilling to permit cooling of the blade during engine operation. The laser drilling to form the cooling holes 14 may be accomplished by any known method, such as by using a laser 16 and a laser beam 18 to drill the holes 14 in the wall 20, through to the hollow interior of the blade 10.

Figure 2:
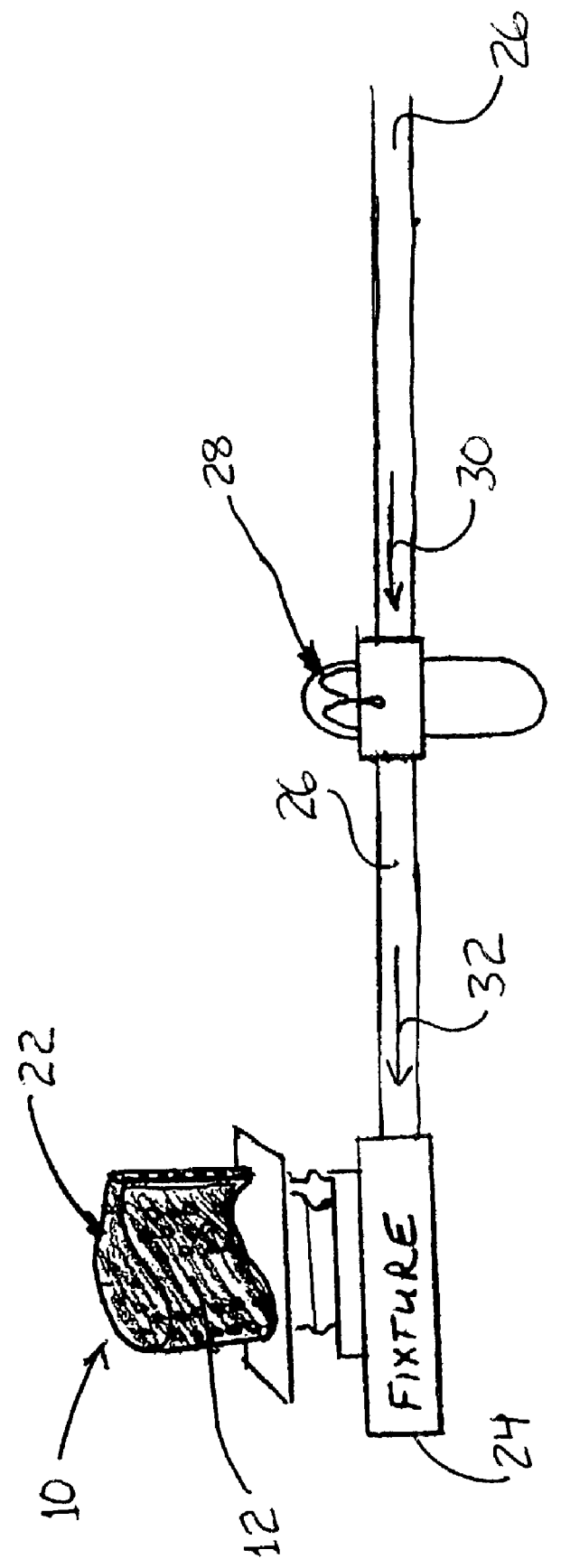
FIG. 2 is a perspective view illustrating the fluorescent cooling hole inspection of the turbine blade illustrated in FIG. 1 in accordance with the present invention.
Figure 3:
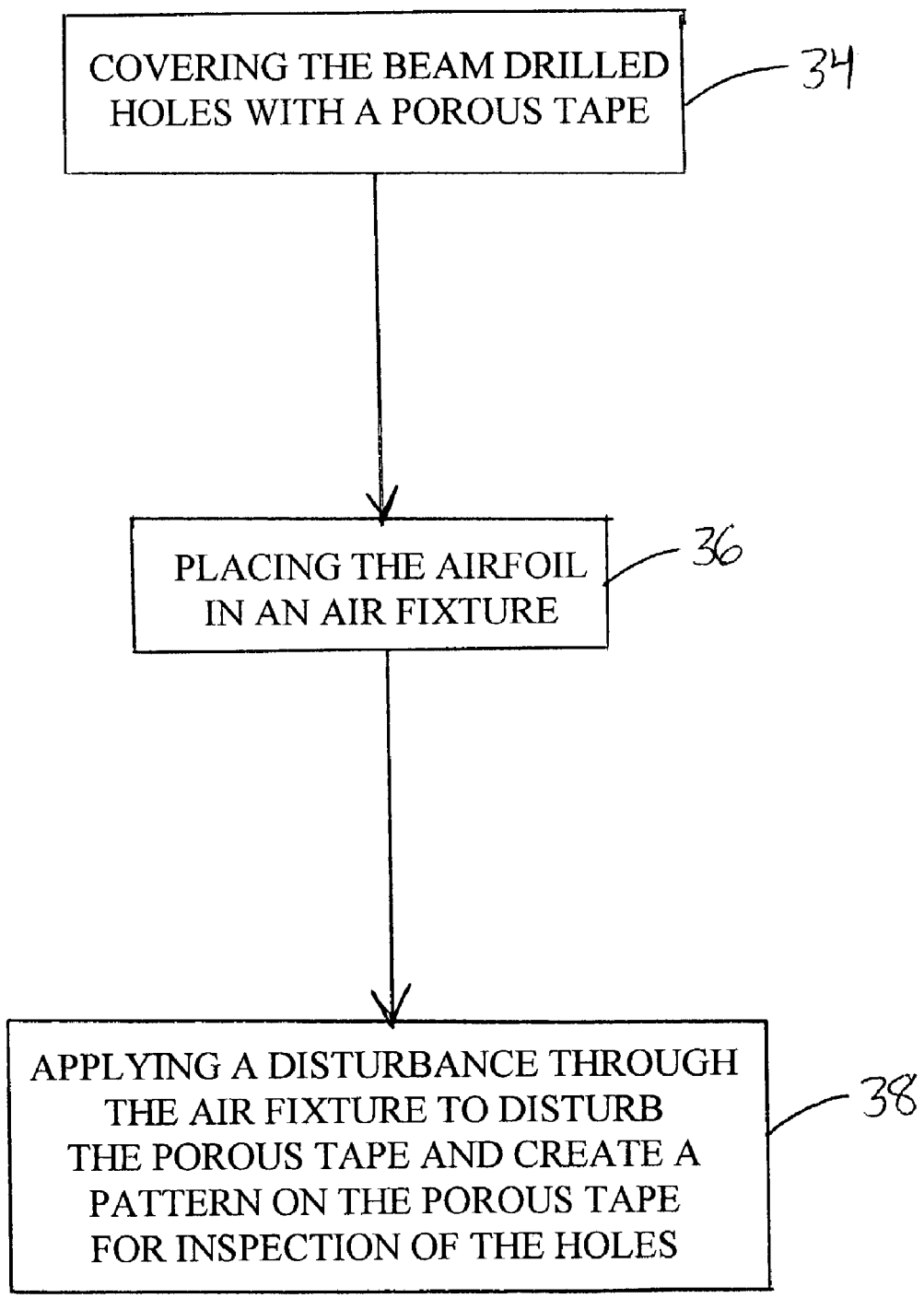
FIG. 3 is a flow chart diagram illustrating a method of fluorescent inspection of the cooling holes in accordance with the present invention.

As illustrated in FIG. 2, a method is provided to inspect the cooling holes 14 to determine if the holes are open to the internal cavity of the blade 10. The holes are inspected to identify not-through or plugged holes. Referring to FIGS. 2 and 3, the cooling holes 14 of a completed, lasered and deburred turbine airfoil 10 are covered with a very porous tape 22, as indicated by step 34 of FIG. 3. The tape may be any suitable porous tape, such as, for example, 3M Vent tape #3394. The turbine airfoil 12 is then placed into an air fixture 24 that has a metered amount of fluorescent liquid, such as, for example, Sherwin Inc. #HM604, dripped into the airline 26. Placement of the airfoil 12 in the air fixture 24 is indicated by step 36 of FIG. 3. Atomizer 28, having fluorescent liquid, receives existing air in the direction indicated by arrow 30. Atomized fluorescent liquid then exits the atomizer 28 and enters the fixture 24, as indicated by arrow 32. The atomized fluorescent liquid flows through the turbine airfoil internal cavities, exiting through the open cooling holes 14, where it is absorbed by the porous tape 22. Step 38 of FIG. 3 illustrates the application of a disturbance, such as the atomized fluorescent liquid, through the air fixture.

A pattern will appear on the tape surface, in the area of all open holes 14. Under black light, the pattern can be inspected to find aberrations in the expected pattern, which may be indicative of no-through or blocked holes. The part can then be inspected for the presence of not-through or plugged holes, which holes have been indicated by the lack of the expected pattern on the tape, corresponding to any not-through or plugged holes. After inspection, the tape 22 can be removed and disposed of in an environmentally safe manner.

The porous tape and fluorescent inspection method disclosed herein has many advantages over cooling hole inspection methods disclosed in the prior art. The method of the present invention is easier and more time-and cost-efficient than methods disclosed in the prior art, allows for black light inspection of cooling holes, and minimizes the time-consuming use of pin check inspection. Furthermore, the inspection method of the present invention can be incorporated into the cellular manufacturing concept.

The present invention also includes the various embodiments of a porous temperature sensitive tape. Such an embodiment could allow for detection of not-through and plugged holes using color change rather than a fluorescent penetrant. For example, after applying the tape to the airfoil surface, hot or cold air can be blown through the airfoil, exiting the holes and activating the tape. A color change in the tape would allow for inspection of the cooling holes pattern. Alternatively, instead of the tape being temperature sensitive, the tape could detect moisture, chemicals, the pH of a liquid, a particulate, and other variants, all in accordance with the teachings of the present invention.

In yet another alternative embodiment of the present invention, the tape can be a thin, flexible tape that would allow for the surface of the tape to be deformed, such as by using pressure. Such an alternative is consistent with the teachings of the present invention and allows for the inspection of the cooling hole pattern.

The cooling hole pattern applied to the tape could be interpreted or read by any suitable means, such as, for example, by human eye or by using a computer software program and a sensing mechanism. The mechanism could visually or mechanically read the tape after the tape has been activated, thereby eliminating the need for the human eye to evaluate the tape. Black light or other light sources can also be applied to assist in the reading of the tape.

While the invention has been described with reference to preferred and exemplary embodiments, it will be understood by those skilled in the art that various changes may be made and equivalents may be substituted for elements thereof without departing from the scope of the invention. The foregoing description and descriptive embodiments have been presented for the purpose of describing and illustrating the invention. It is not intended to be exhaustive or to limit the invention. Obviously, many modifications and variations are possible in light of the above teachings, without departing from the scope of the invention. Therefore, it is intended that the invention not be limited to the particular embodiment disclosed as the best mode contemplated for carrying out this invention, but that the invention desired to be secured will include all embodiments and modifications as fall within the true spirit and scope of the appended claims.

What is claimed is:

1. A method for inspecting beam drilled holes in a wall of an article with a hollow interior, said method comprising the steps of:
    covering the beam drilled holes with a porous tape;
    placing the article in an air fixture; and
    applying a disturbance through the air fixture to disturb the porous tape, thereby creating a pattern on the porous tape indicative of not-through or plugged holes.

2. A method as claimed in claim 1 wherein the article comprises a turbine airfoil.

3. A method as claimed in claim 2 wherein the disturbance comprises an atomized fluorescent liquid.

4. A method as claimed in claim 3 further comprising the step of inspecting the porous tape under black light.

5. A method for inspecting beam drilled cooling holes in a turbine airfoil of a gas turbine engine blade, said method comprising the steps of:
    covering the beam drilled holes with a porous tape;
    placing the turbine airfoil in an air fixture that has a metered amount of fluorescent liquid dripped into an associated airline; and
    flowing the atomized fluorescent liquid through an internal cavity of the turbine airfoil to exit the beam drilled cooling holes, thereby creating a pattern on the porous tape indicative of not-through or plugged holes.

6. A method as claimed in claim 5 further comprising the step of inspecting the porous tape under black light.

7. A system for inspecting beam drilled holes in a wall of an article with a hollow interior, comprising:
    a porous tape for covering the beam drilled holes;
    an air fixture for receiving the article; and
    a disturbance applied through the air fixture to disturb the porous tape, thereby creating a pattern on the porous tape indicative of not-through or plugged holes.

8. A system as claimed in claim 7 wherein the article comprises a turbine airfoil.

9. A system as claimed in claim 8 wherein the disturbance comprises an atomized fluorescent liquid.

10. A system as claimed in claim 9 further comprising a black light for inspecting the porous tape to detect the presence of not-through or plugged holes.

* * * * *